(12) United States Patent  
Kitagawa et al.

(10) Patent No.: US 7,647,847 B2  
(45) Date of Patent: Jan. 19, 2010

(54) LIQUID SAMPLE SUCTIONING DEVICE AND ANALYZER

(75) Inventors: Nobuhiro Kitagawa, Akashi (JP); Shuhei Kaneko, Kobe (JP)

(73) Assignee: Sysmex Corporation, Kobe-shi (JP)

( * ) Notice: Subject to any disclaimer, the term of this patent is extended or adjusted under 35 U.S.C. 154(b) by 290 days.

(21) Appl. No.: 11/516,278

(22) Filed: Sep. 5, 2006

(65) Prior Publication Data

US 2007/0062316 A1 Mar. 22, 2007

(30) Foreign Application Priority Data

Sep. 5, 2005 (JP) .............................. 2005-256353

(51) Int. Cl.  
*G01N 1/00* (2006.01)

(52) U.S. Cl. .................................................. 73/864.86

(58) Field of Classification Search ............. 73/864.01, 73/864.86, 864.11, 864.21; 422/62, 100; 436/43

See application file for complete search history.

(56) References Cited

U.S. PATENT DOCUMENTS

| 3,872,730 | A | * | 3/1975 | Ringrose et al. ......... 73/864.23 |
| 4,515,752 | A | * | 5/1985 | Miramanda ................... 422/99 |
| 4,721,137 | A | | 1/1988 | Müller ......................... 141/65 |
| 4,951,512 | A | | 8/1990 | Mazza et al. ............. 73/864.23 |
| 5,132,088 | A | | 7/1992 | Wakatake ..................... 422/63 |
| 5,935,523 | A | * | 8/1999 | McCandless et al. ........ 422/100 |
| 6,818,182 | B2 | * | 11/2004 | Le Comte et al. ............. 422/65 |
| 2005/0223822 | A1 | * | 10/2005 | Ozbal ...................... 73/864.41 |

* cited by examiner

*Primary Examiner*—Hezron Williams  
*Assistant Examiner*—Tamiko D Bellamy  
(74) *Attorney, Agent, or Firm*—Brinks Hofer Gilson & Lione (57) ABSTRACT

The present invention provides a liquid sample suctioning device capable of simplifying a structure thereof, preventing clogging of a pipette and contamination of a liquid sample, and closing a hole formed in a lid after the liquid sample is suctioned. The liquid sample suctioning device is adapted to suction the liquid sample in the container by piercing through the lid mounted on an opening of the container, comprising a piercer having a leading end insertable into the container by piercing through the lid and forming a deformation piece deformable toward an inner side of the container in the lid, a pipette configured for suctioning the liquid sample in the container, a first driving part for moving up and down the piercer, and a second driving part for moving up and down the pipette along the piercer.

18 Claims, 11 Drawing Sheets

LIQUID SAMPLE SUCTIONING DEVICE AND ANALYZER

This application claims priority under 35 U.S.C. § 119 to Japanese Patent Application No. JP2005-256353 filed Sep. 5, 2005, the entire content of which is hereby incorporated by reference.

FIELD OF THE INVENTION

The present invention relates to a liquid sample suctioning device and an analyzer comprising the liquid sample suctioning device.

BACKGROUND

An analyzer for suctioning a liquid sample stored in a sealed container such as a vacuum blood collection tube and analyzing the suctioned liquid sample is widely known. A conventional analyzer of this type comprises a suction tube whose leading end is sharpened in order to suction the liquid sample from the sealed container, wherein the suction tube is adapted to pierce through a lid of the sealed container. The suction tube adapted in the foregoing manner, however, has the problem that scraped pieces generated when the suction tube pierces through the lid invade the suction tube, thereby unfavorably clogging the suction tube.

In order to solve the foregoing problem, a sampling device adapted to thrust a hole making tube into a lid and insert a suction tube through the hole making tube to thereby insert a leading end of the suction tube into a sealed container was disclosed (see U.S. Pat. Nos. 4,951,512 and 5,132,088). As another example, a device provided with a hole making tool having a sharp leading end and a suction tube was disclosed (U.S. Pat. No. 4,721,137). The device is adapted to form a hole in a lid using the hole making tool, and thereafter move the suction tube to be positioned with respect to the hole so that the suction tube is inserted through the hole. These devices can prevent the suction tube from being clogged with the scraped pieces.

However, the devices having the structures disclosed in U.S. Pat. Nos. 4,951,512 and 5,132,088 have the disadvantages that the hole making tube was clogged with the scraped pieces when it was thrust into the lid, and the scraped pieces entered the liquid sample in the sealed container, thereby clogging the suction tube and contaminating the liquid sample. As another disadvantage, the hole making tube, through which the suction tube was to be inserted, was inevitably increased in size, and the hole formed in the lid by the thrust of the hole making tube was thereby increased in size. When the hole is too large, the hole may not be closed after the hole making tube is removed from the lid, and a large force was conventionally required to push the hole making tube into the lid.

A disadvantage included in the constitution disclosed in U.S. Pat. No. 4,721,137 which required the positioning of the suction tube with respect to the hole in the lid after the hole making tool was thrust into the lid of the sealed container and then removed from the lid. It was necessary to firmly retain the sealed container so that there was no positional deviation of the sealed container when the hole making tool was removed. In order to realize such a firm retention, a structure for retaining the sealed container unfavorably became complicated, and a user had to make a lot of operations when he/she set the sealed container in the device.

SUMMARY OF THE INVENTION

The scope of the present invention is defined solely by the appended claims, and is not affected to any degree by the statements within this summary.

The first aspect of the present invention relates to a liquid sample suctioning device for suctioning a liquid sample in a container comprising a lid, comprising:

a piercer having a leading end insertable into the container by piercing through the lid and forming a deformation piece deformable toward an inner side of the container in the lid;

a pipette configured for suctioning the liquid sample in the container;

a first driving part for moving up and down the piercer; and a second driving part for moving up and down the pipette along the piercer.

The second aspect of the present invention relates to a liquid sample suctioning device for suctioning a liquid sample in a container comprising a lid, comprising:

a first piercer having a leading end insertable into the container by piercing through the lid and forming a slit in the lid;

a second piercer comprising a needle part configured for piercing the lid at a leading end thereof and for suctioning the liquid sample in the container;

a first driving part for moving up and down the first piercer; and a second driving part for moving up and down the second piercer.

The third aspect of the present invention relates to a liquid sample suctioning device for suctioning a liquid sample in a container comprising a lid, comprising:

a piercer having a leading end insertable into the container by piercing through the lid and forming a linear slit in the lid;

a pipette configured to be inserted into the container and suction the liquid sample in the container;

a first driving part for moving up and down the piercer; and a second driving part for moving up and down the pipette when the piercer pierces through the lid.

The fourth aspect of the present invention relates to an analyzer, comprising:

a liquid sample suctioning unit for suctioning a liquid sample in a container comprising a lid; and an analyzing unit for analyzing the liquid sample suctioned by the liquid sample suctioning unit, wherein the liquid sample suctioning unit comprises:

a piercer having a leading end insertable into the container by piercing through the lid and forming a deformation piece deformable toward an inner side of the container in the lid;

a pipette configured for suctioning the liquid sample in the container;

a first driving part for moving up and down the piercer; and a second driving part for moving up and down the pipette along the piercer.

The fifth aspect of the present invention relates to an analyzer, comprising:

a liquid sample suctioning unit for suctioning a liquid sample in a container comprising a lid; and an analyzing unit for analyzing the liquid sample suctioned by the liquid sample suctioning unit, wherein the liquid sample suctioning unit comprises:

a first piercer having a leading end insertable into the container by piercing through the lid and forming a slit in the lid;

a second piercer comprising a needle part configured for piercing the lid at a leading end thereof and for suctioning the liquid sample in the container;

a first driving part for moving up and down the first piercer; and a second driving part for moving up and down the second piercer.

The sixth aspect of the present invention relates to an analyzer, comprising:

a liquid sample suctioning unit for suctioning a liquid sample in a container comprising a lid; and an analyzing unit for analyzing the liquid sample suctioned by the liquid sample suctioning unit, wherein the liquid sample suctioning unit comprises:

a piercer having a leading end insertable into the container by piercing through the lid and forming a linear slit in the lid;

a pipette configured to be inserted into the container and suction the liquid sample in the container;

a first driving part for moving up and down the piercer; and a second driving part for moving up and down the pipette when the piercer pierces through the lid.

DESCRIPTION OF THE PREFERRED EMBODIMENTS

Hereinafter, embodiments of a liquid sample suctioning device (hereinafter, simply referred to also as suctioning device) according to the present invention and an analyzer comprising the liquid sample suctioning device are specifically described referring to the drawings.

Figure 1:
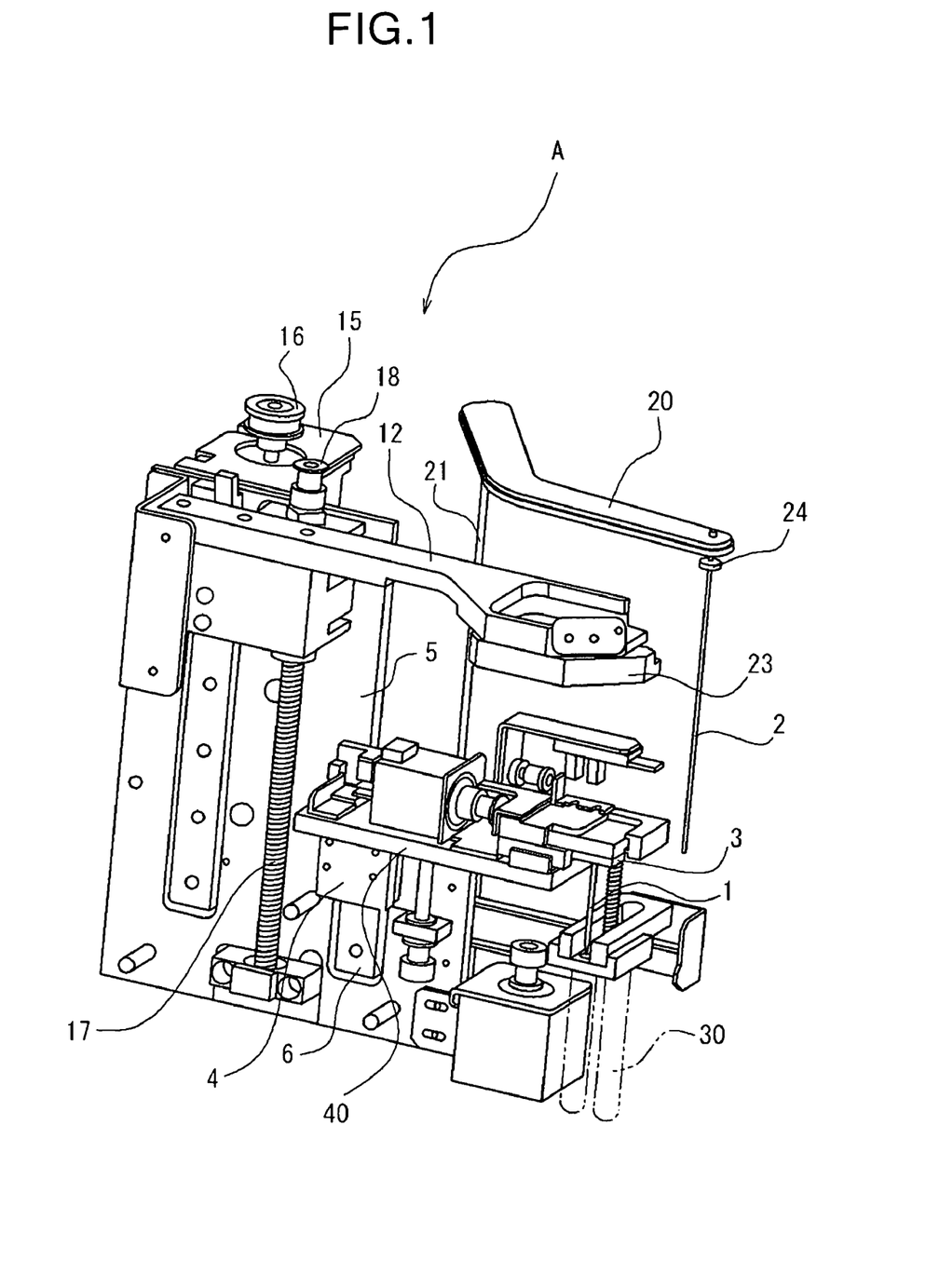
FIG. 1 is a perspective view illustrating a main part of a suctioning device according to an embodiment of the present invention.
Figure 2:
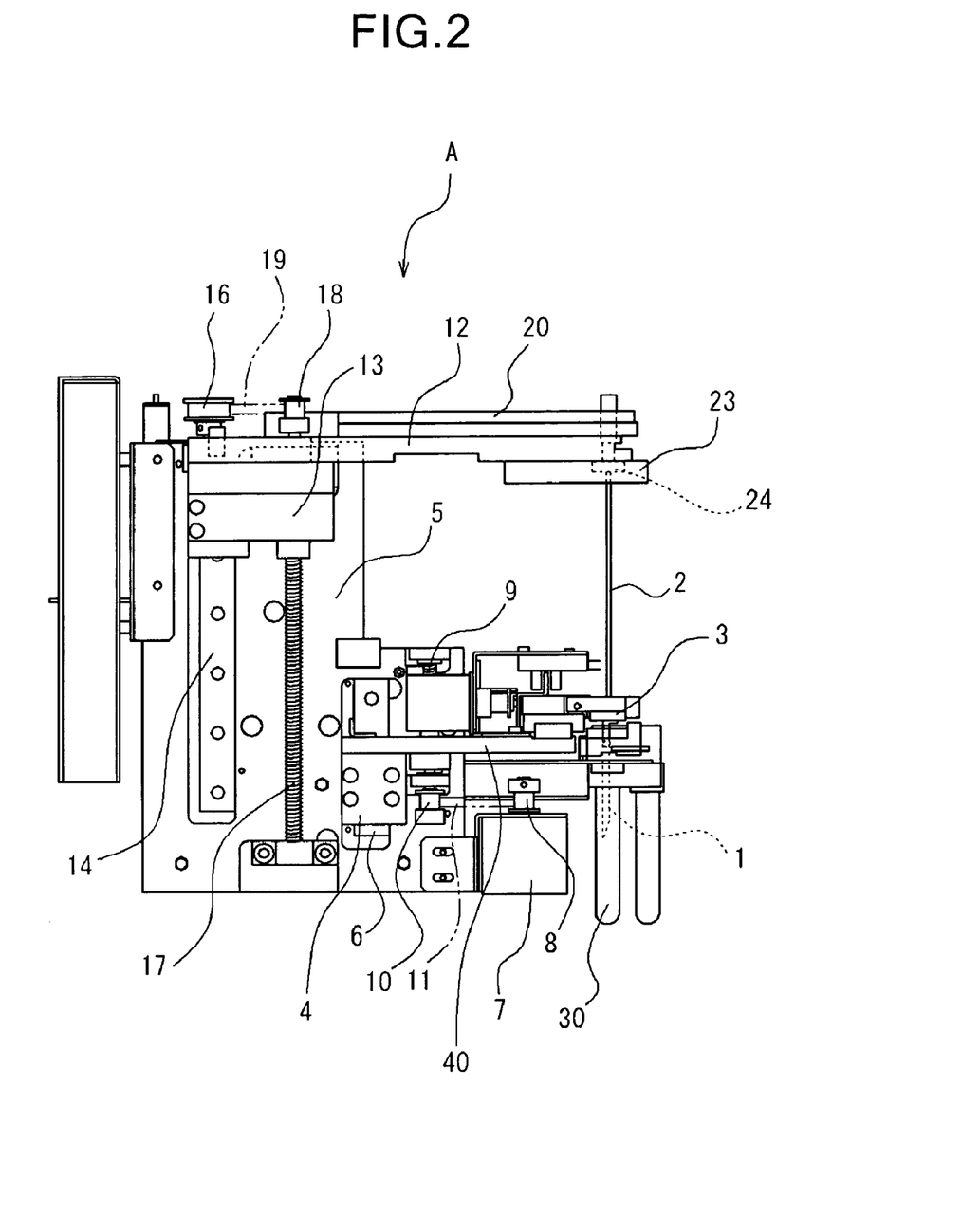
FIG. 2 is a front view illustrating the suctioning device according to the embodiment showing a state where a specimen arm is rotated and engaged with a CP arm after a piercer pierces a lid of a sealed container.
Figure 3:
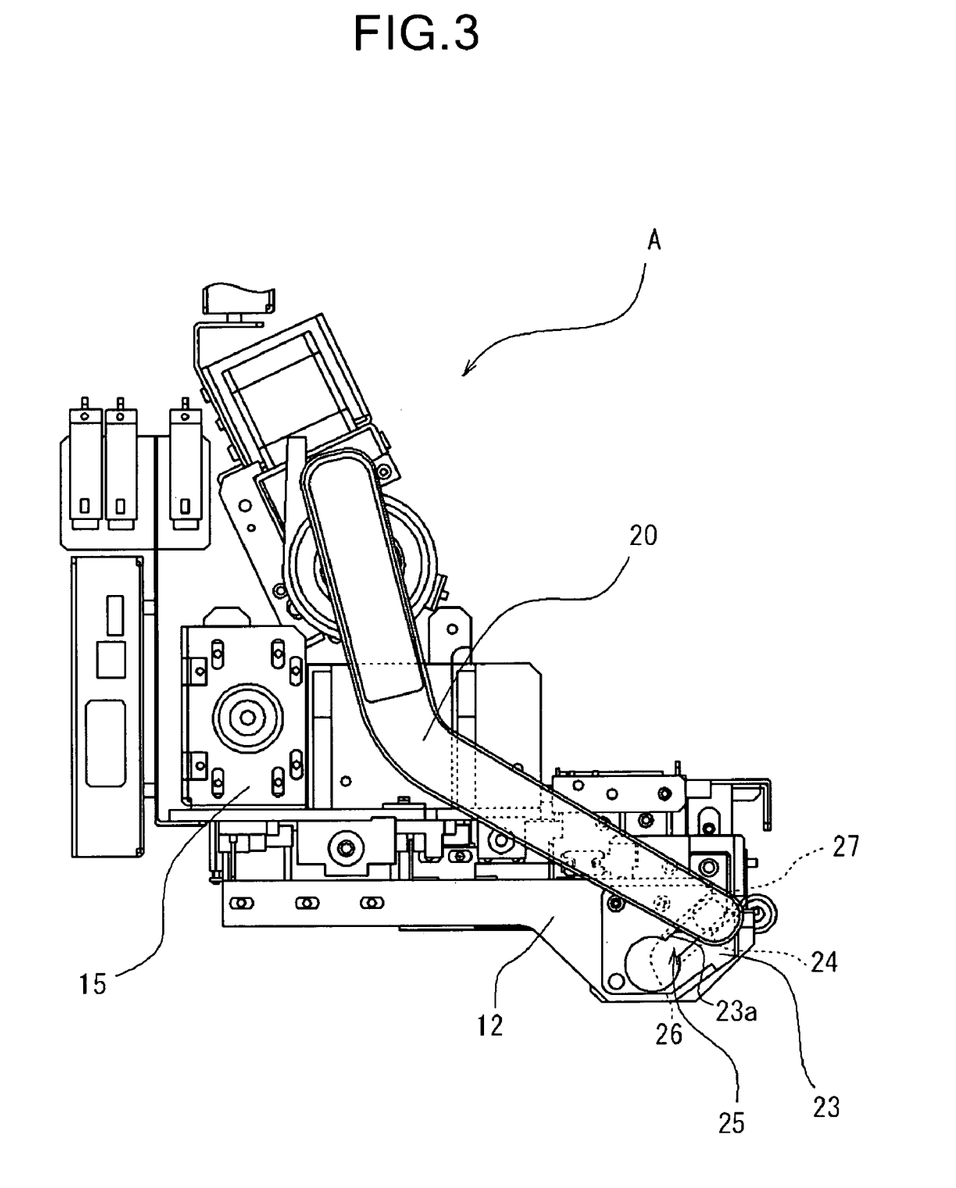
FIG. 3 is a plan view illustrating the state shown in FIG. 2.
Figure 4:
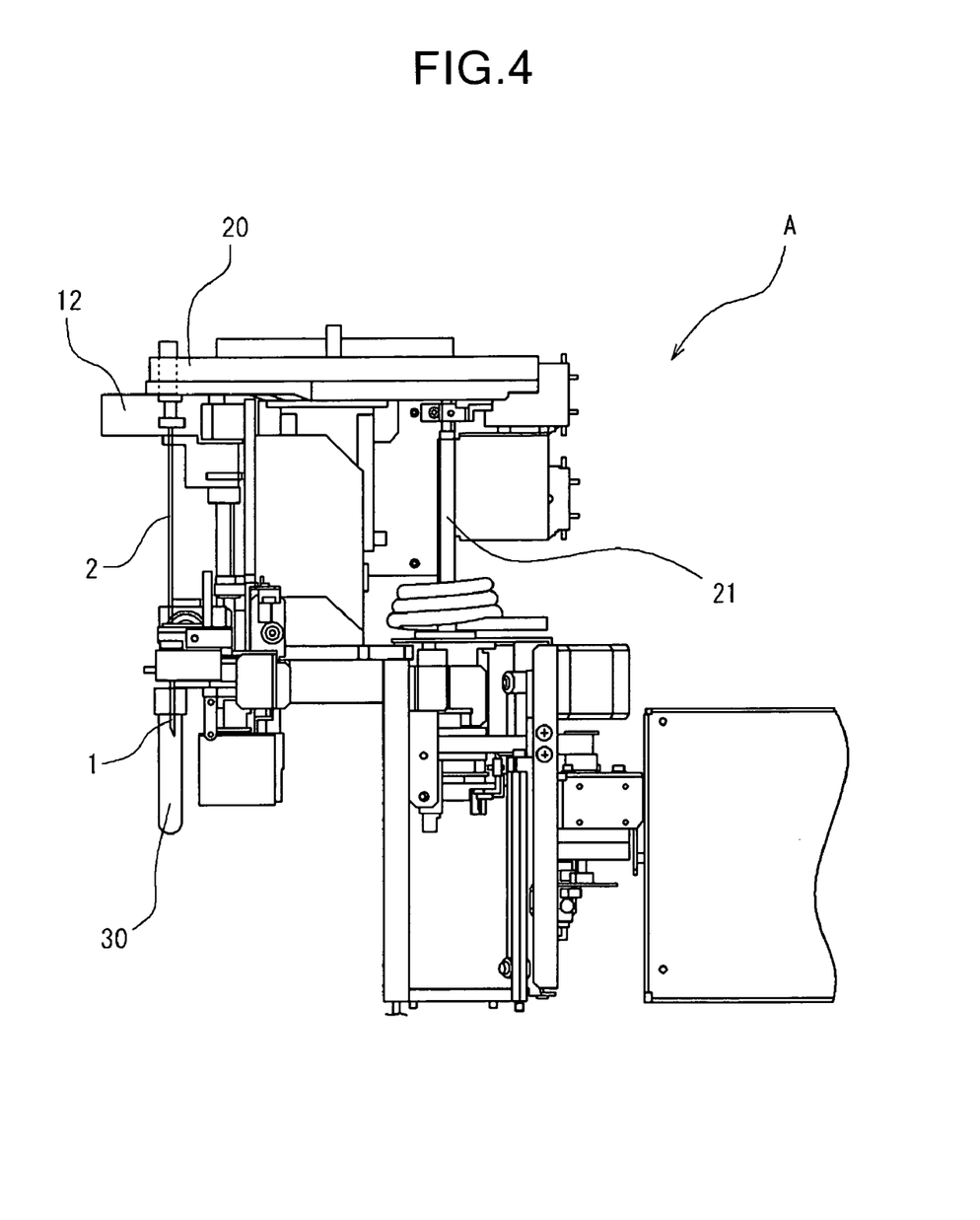
FIG. 4 is a right-side view illustrating the state shown in FIG. 2.
Figure 5:
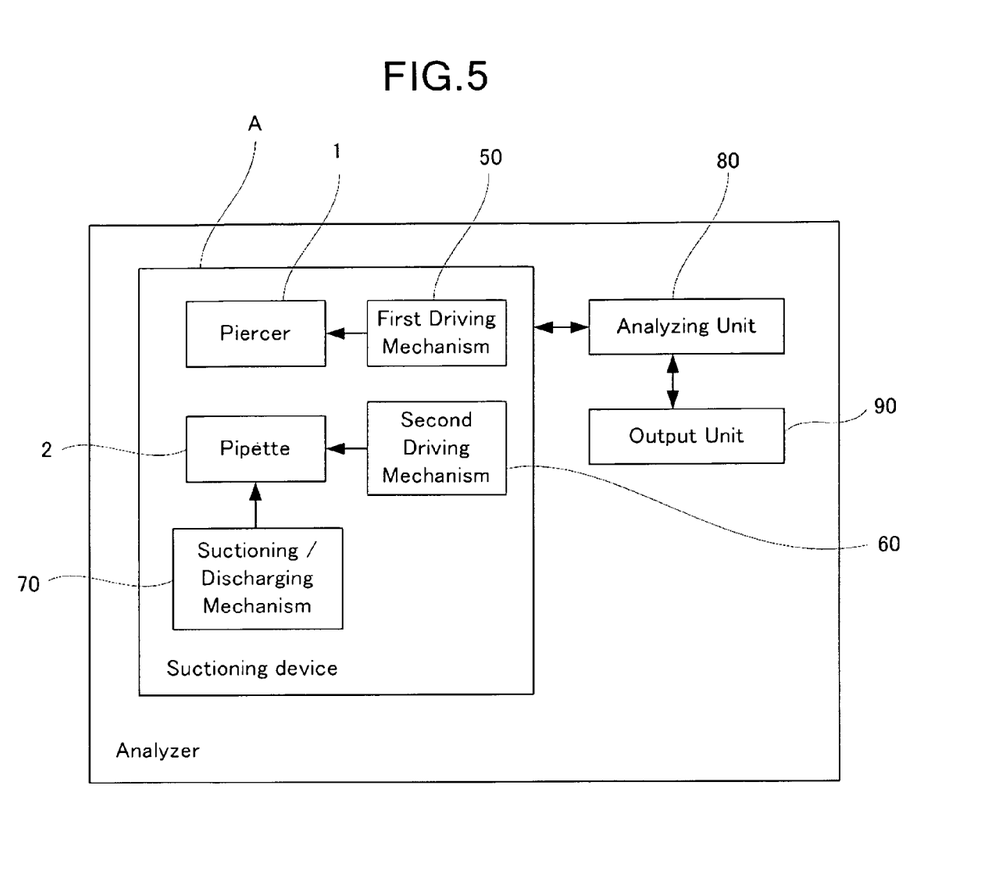
FIG. 5 is a block diagram showing the analyzer according to the embodiment of the present invention.

FIG. 1 is a perspective view illustrating a main part of a suctioning device according to the embodiment. FIG. 2 is a front view illustrating the suctioning device according to the embodiment, which shows a state where a specimen arm is rotated and engaged with a CP arm after a piercer pierces a lid of a sealed container. FIG. 3 is a plan view illustrating the state shown in FIG. 2. FIG. 4 is a right-side view illustrating the state shown in FIG. 2. The suctioning device A is used for suctioning a sample, such as blood or urine, from a sample container 30 (hereinafter, simply referred to also as container) sealed with a lid such as a rubber cap and constitutes a part of a measuring device or analyzer such as a blood coagulation measuring device used for examination of blood coagulation reaction, a blood analyzer for measuring number of erythrocytes and leucocytes in blood, or the like. FIG. 5 is a block diagram showing the analyzer according to the embodiment. The analyzer comprises, other than the suctioning device A, an analyzing unit 80 for analyzing a liquid sample suctioned by the suctioning device A and an output unit 90 for outputting a result of the analysis made by the analyzing unit 80.

The suctioning device A, whose leading end can be inserted into the container 30, mainly consisted of a piercer 1 for forming a deformation piece deformable toward an inner side of the container 30 in the lid, a pipette 2 capable of suctioning the sample in the container 30, a first driving mechanism 50 including a motor for driving the piercer 1, a second driving mechanism 60 including a motor for driving the pipette 2, and a suctioning/discharging mechanism 70 including a syringe pump for suctioning and discharging the sample.

The suctioning device A, whose leading end can be inserted into the container 30, has a piercer 1 for forming a deformation piece deformable toward an inner side of the container 30 in the lid, a pipette 2 capable of suctioning the sample in the container 30, a first driving mechanism 50 including a motor for driving the piercer 1 , a second driving mechanism 60 including a motor for driving the pipette 2, and a suctioning/discharging mechanism 70 including a syringe pump for suctioning and discharging the sample.

The pipette 2 is formed from a thin tube having a passage 2a (see FIG. 7) for the sample therein, and a root-side end of the pipette 2 is held by a specimen arm 20. The pipette 2 is connected to the suctioning / discharging mechanism via a tube or a valve. The leading end of the pipette 2 is preferably formed in a tapered shape, as shown in FIG. 7A, so that an amount of the sample attached to the leading end of the pipette when the sample is suctioned can be decreased. As a result, the accuracy in the amount of the suctioned sample can be increased, which leads to an improvement in the accuracy of the sample analysis.

The piercer 1 and the pipette 2 are simultaneously placed in a washing spitz (not shown), and a washing solution is injected from a lower lateral direction of the washing spitz and suctioned from an upper lateral direction thereof so that the piercer 1 and the pipette 2 can be washed. As a result, the washing step can be simplified as compared with a conventional sample suction tube comprising double tubes.

The specimen arm 20 is a member which holds or retains the pipette 2 to thereby move the pipette 2 between a sample suctioning position and a sample discharging position, and is adapted to freely rotate around a shaft 21 provided in the vicinity of one end thereof and freely move upward and downward.

The retaining block 3 for retaining the piercer 1 is made from a plate member formed from synthetic resin such as ABS resin, and the mounting section 1b of the pipette 1 is secured to a peripheral wall of an opening of the retaining block 3. One end of a base 40 whose other end is provided with the retaining block 3 (left-side end in FIG. 2) is provided with a first guide member 4 having a rectangular shape, on an surface of which (surface on the rear side of the paper in FIG. 2) a groove part is formed. The groove part of the first guide member 4 is fitted into a first elongated member 6 vertically fixed in a casing 5 of the suctioning device A, and the vertical movement of the base 40 is thereby guided.

At a lower part of the base 40, a motor 7, which is a driving source for moving the base 40 upward and downward, is provided. An output shaft of the motor 7 is provided with a driving pulley 8. A belt 11 bridges the driving pulley 8 and a driven pulley 10 provided at a lower end of a first screw 9 retained in the casing 5 rotatably. The first screw 9 is screwed into a female screw part (not shown) formed in the base 40. When the first screw 9 is rotated, the base 40 can move upward and downward.

At an upper part of the base 40, a CP arm 12 adapted to be engaged with the specimen arm 20 to thereby move the specimen arm 20 upward and downward is provided. One end of the CP arm (left-side end in FIG. 2) is provided with a second guide member 13 having a rectangular shape, on a surface of which (surface on the rear side of the paper in FIG. 2) a groove part is formed, in a manner similar to the base 40. The groove part of the second guide member 13 is fitted into a second elongated member 14 vertically fixed in the casing 5 of the suctioning device A, and the vertical movement of the CP arm 12 is thereby guided.

A motor 15, which is a driving source for moving the CP arm 12 upward and downward, is provided in the casing 5. An output shaft of the motor 15 is provided with a driving pulley 16, and a belt 19 bridges the driving pulley 16 and a driven pulley 18 provided at an upper end of a second screw 17 retained in the casing 5 rotatably. The second screw 17 screwed into a female screw part (not shown) formed in the CP arm 12. When the second screw 17 is rotated, the CP arm 12 can move upward and downward.

An engaging section 23 for holding the specimen arm 20 is formed at one end of the CP arm 12 (right-side end in FIG. 2) so that the specimen arm 20 is moved upward and downward. The engaging section 23 has an introduction slit 25 for receiving an engaging member 24 having a disc shape and provided in the vicinity of the root-side end of the pipette 2. A groove 26 having a width slightly larger than a thickness of the engaging member 24 is formed on a side surface 23a of the engaging section 23 constituting the introduction slit 25. When the specimen arm 20 is rotated clockwise around the shaft 21 as a center of the rotation, the engaging member 24 having the disc shape is introduced into the groove 26. A chamfer 27 is formed on an inlet side of the introduction slit 25 in order to smoothly introduce the engaging member 24 into the groove 26.

Next, a suctioning operation using the suction device thus constituted is described.

1) In an initial state, the piercer 1 is at an elevated position, and the specimen arm 20 for holding the pipette 2 is not engaged with the CP arm 12 yet as shown in FIG. 1. When the container in which the sample is stored is transported to a lower part of the piercer 1 by a transportation mechanism (not shown), the motor 7 is rotated. The rotation is transmitted to the first screw 9 via the driving pulley 8, belt 11 and driven pulley 10, and the first screw 9 is thereby rotated. Accordingly, the base 40 having the female screw part screwed into the first screw 9 moves downward under the guidance by the first guide member 4 and the first elongated member 6, and the piercer 1 pierces the lid of the container. As a result, the deformation piece is formed in the lid mounted on the opening of the container.

2) Next, the specimen arm 20 is rotated clockwise around the shaft 21 as the center of the rotation, and the engaging member 24 having the disc shape is thereby introduced into the groove 26 as shown in FIG. 3 (Engagement of the specimen arm 20 and the CP arm 12).

3) Then, the motor 15 is rotated. The rotation is transmitted to the second screw 17 via the driving pulley 16, belt 19 and driven pulley 18, and the second screw 17 is thereby rotated. Accordingly, the CP arm 12, which has the female screw part screwed into the second screw 17, moves downward under the guidance by the second guide member 13 and the second elongated member 14. Then, the specimen arm 20 also moves downward in conjunction with the CP arm 12 because the engaging member 24 of the specimen arm 20 is located in the groove 26 of the engaging section 23, and the pipette 2 is thereby inserted into the container. At the time, the pipette 2 is inserted into the container under the guidance of the piercer 1. The deformation piece formed by the piercer 1 can be deformed toward the inner side of the container, and the deformation piece is deformed then the pipette 2 is moved so that the leading end of the pipette 2 abuts against the deformation piece. Therefore, the pipette 2 can be inserted to reach a predetermined position in the container with a small force. When the pipette 2 is inserted into the container, external air can be communicated with the inside of the container via a gap or a passage generated by the deformation of the deformation piece, which easily exposes the inside of the container to the external air.

Because of the guidance by the piercer 1, the pipette 2 can be prevented from any deformation caused by a reaction force from the deformation piece when inserted into the container. In other words, a thin pipette can be used, which decreases the amount of the sample attached to the leading end of the pipette when the sample is suctioned. As a result, the accuracy in the amount of the suctioned sample can be increased, which favorably improves the accuracy in the sample analysis.

Because the deformation piece is deformed so that the pipette 2 can be inserted into the container in the state where the lid is pierced by the piercer 1, a possible deformation of a pad of the lid oppositely facing the deformation piece is regulated by the piercer 1. As a result the deformation piece can be easily deformed, and the pipette 2 can be thereby easily inserted into the container.

The formation of the deformation piece in the lid by the piercer 1 can advantageously avoid generation of scraped pieces in the lid to thereby prevent clogging of the pipette 2 and contamination of the liquid sample. Further, when the deformation piece regains its original state after the liquid sample is suctioned, the hole formed in the lid can be closed.

Next, the suctioning/discharging mechanism, such as the syringe pump, is driven, and the sample in the container is suctioned by means of the pipette 2. Because the pipette 2 is used in order to suction the sample, a dead volume of the sample can be minimized even when the opening of the sample container is sealed with the lid.

5) When the suction is completed, the motor 15 is rotated in a direction reverse to that of the foregoing rotation so that the CP arm 12 moves upward. Thereby, the pipette 2 is lifted out of the container.

6) When the CP arm 12 moves upward to reach a predetermined position, the specimen arm 20 is rotated anticlockwise around the shaft 21. Accordingly, the engaging member 24 is disengaged from the groove 26, which releases the engagement between the CP arm 12 and the specimen arm 20.

7) When the CP arm 12 moves upward to reach the predetermined position, the motor 7 is rotated in a direction reverse to that of the foregoing rotation, which moves the piercer 1 upward.

The sample suctioned into the pipette 2 is discharged into a container such as a cuvette or a mixing chamber, and then, diluted with a diluting solution, mixed with a predetermined sample agent, and the like. The sample subjected to these steps is then analyzed and measured.

Another embodiment of the present invention is described below. In the suctioning device according to the embodiment described earlier, the deformation piece is formed in the lid by means of the piercer 1 having the substantially L-letter shape in section. Such a piercer can be replaced with a flat piercer.

Figure 6:
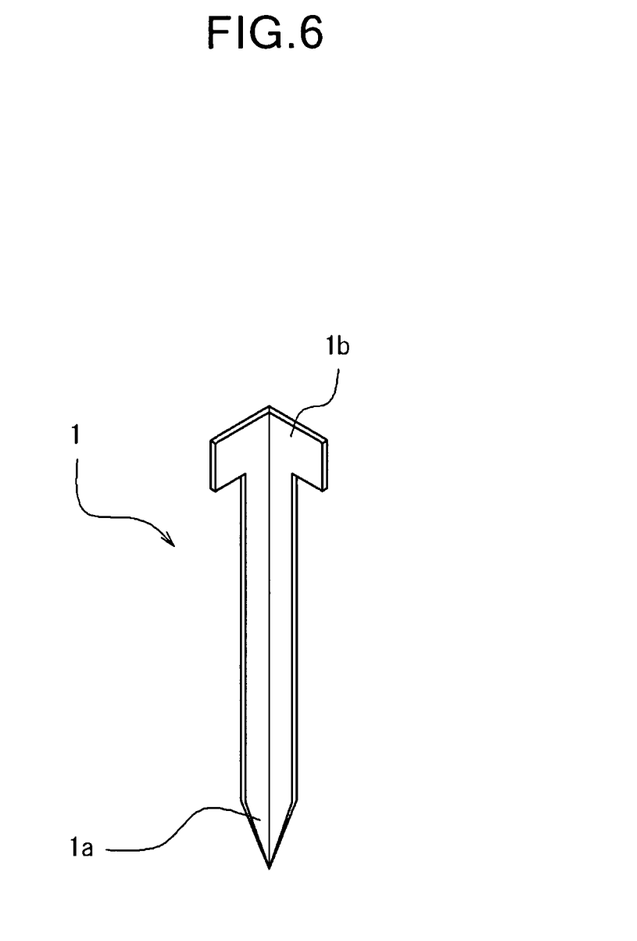
FIG. 6 is an illustration of an example of the piercer used when a deformation piece is formed.
Figure 8:
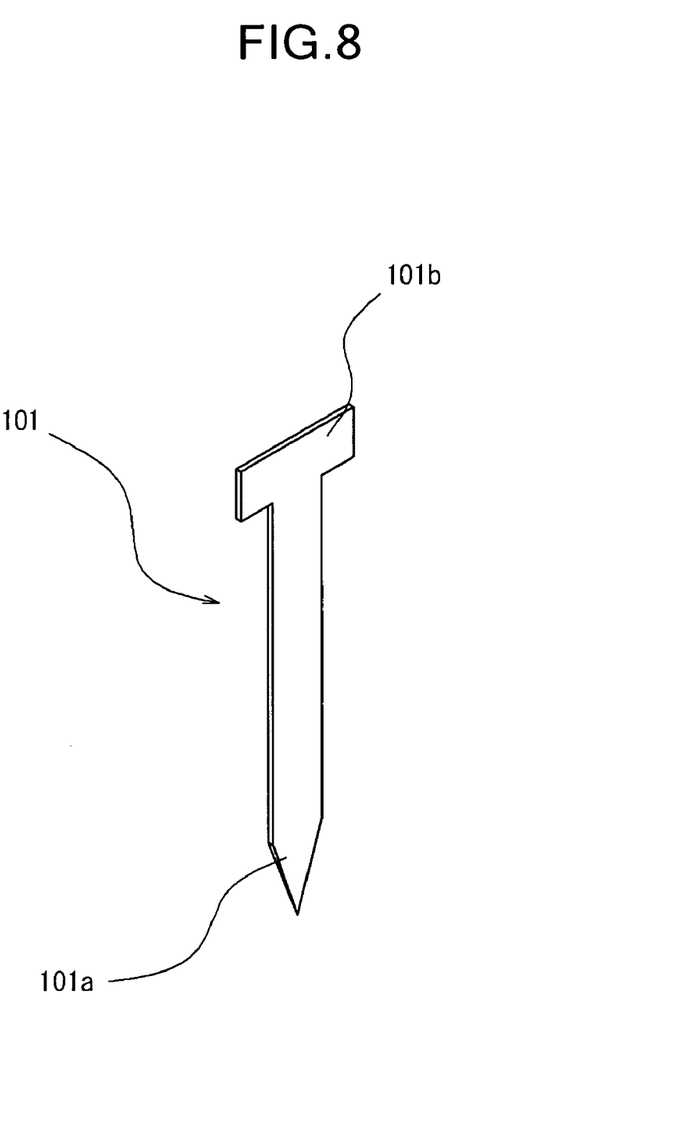
FIG. 8 is an illustration of an example of a first piercer used when the lid is pierced.

FIG. 8 shows an example of the flat piercer. A shape blade section 101*a* capable of piercing the lid is formed at one end of a piercer 101, while a mounting section 101*b* secured to a retaining block for retaining the piercer 101 is formed at another end thereof. When the piercer 101 pierces the lid of the container, the deformation piece is not formed in the lid, but only a linear slit is formed, which is different to the piercer 1 shown in FIG. 6. In the structure in which it is difficult to insert the pipette into the container, the sample is suctioned by means of a piercer having a needle part at a leading end thereof.

Figure 9:
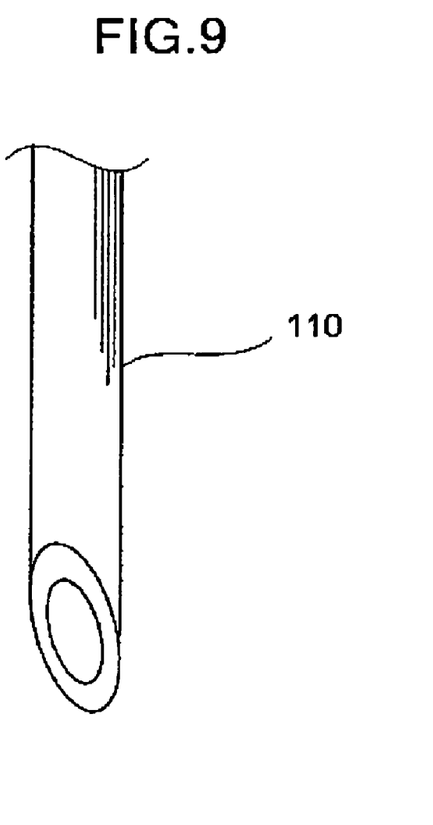
FIG. 9 is an illustration of an example of a second piercer.

More specifically, the suctioning device according to another embodiment comprises a first piercer (piercer 101) having a leading end insertable into the container and capable of forming the slit in the lid and a second piercer 110 (see FIG. 9) provided with a needle part capable of piercing the lid at a leading end thereof and capable of suctioning the liquid sample in the container. In the suctioning device, before the piercer 110 (second piercer) which suctions the sample in the container pierces the lid, the slit is formed in the lid by means of the other piercer 101 (first piercer). Therefore, a part of the lid in which the slit is formed is deformed when the second piercer 110 pierces the lid, which communicates the external air and the inside of the container. As a result, the inside of the container can be easily exposed to the external air. In the suctioning device thus constituted, the second piercer 110 is preferably capable of piercing the lid in the state where the first piercer 101 pierces the lid. In such a constitution, the deformation of the part of the lid on the opposite side of the part of the lid pierced by the second piercer 110 with the first piercer 101 sandwiched therebetween is regulated by the first piercer 101. Accordingly, the part of the lid pierced by the second piercer 110 can be easily deformed, and the second piercer 110 can thereby easily pierce into the container. The second piercer 110 is preferably guided by the first piercer 101 when the lid is pierced. The guidance by the first piercer 101 can prevent the second piercer 110 from any deformation caused by a reaction force from the lid when the lid is pierced. In other words, a thin second piercer 110 can be used, which decreases the amount of the sample attached to the leading end of the second piercer 110 when the sample is suctioned. As a result, the accuracy of the amount of the suctioned sample can be increased, which favorably improves the accuracy in the sample analysis.

In the present embodiment, the scraped pieces of the lid are not generated because the slit is formed in the lid by the first piercer, and the clogging of the second piercer and the contamination of the liquid sample generated thereby can be prevented. Further, when the part of the lid where he slit is formed recovers to its original state after the liquid sample is suctioned, the hole formed in the lid can be closed.

In the case of the insertion with respect to the container in the state where the lid is pierced by the piercer, the pipette can be used in place of the second piercer. More specifically, the suctioning device according to the present invention may comprise the piercer having the leading end insertable into the container and forming the linear slit in the lid, and the pipette inserted into the container in the state where the lid is pierced by the piercer forming a linear slit in the lid and a pipette capable of suctioning the liquid sample in the container.

In the present embodiment, the linear slit part formed by the piercer is deformed when the pipette is inserted into the lid, which communicates the external air and the inside of the container. As a result, the inside of the container can be easily exposed to the external air. Further, the pipette is inserted into the container in the state where the lid is pierced by the piercer so that the slit is easily deformed by the piercer. As a result, the pipette can be easily inserted into the container.

Further, the formation of the linear slit in the lid by the piercer can avoid the generation of the scraped pieces in the lid, and the clogging of the pipette and thereby the contamination of the liquid sample can be prevented. Further, when the part of the lid where the slit is formed recovers to its original state after the liquid sample is suctioned, the hole formed in the lid can be closed.

Figure 7:
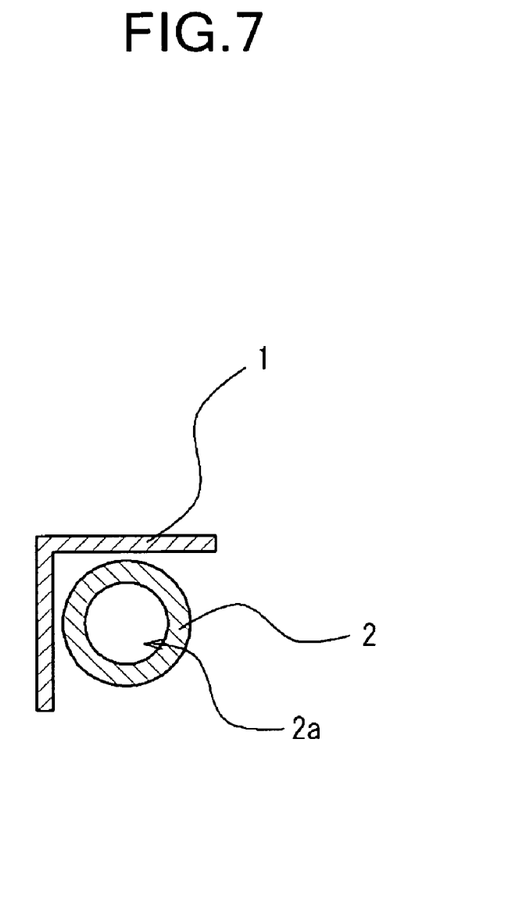
FIG. 7 is a sectional view illustrating the piercer shown in FIG. 5 and a pipette used together with the piercer shown in FIG. 5.
Figure 7A:
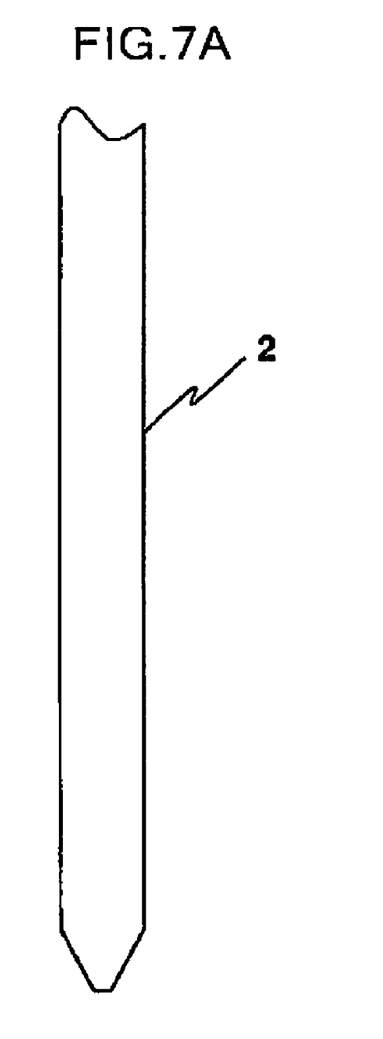
FIG. 7A is a sectional view illustrating a piercer formed in a tapered shape.
Figure 10:
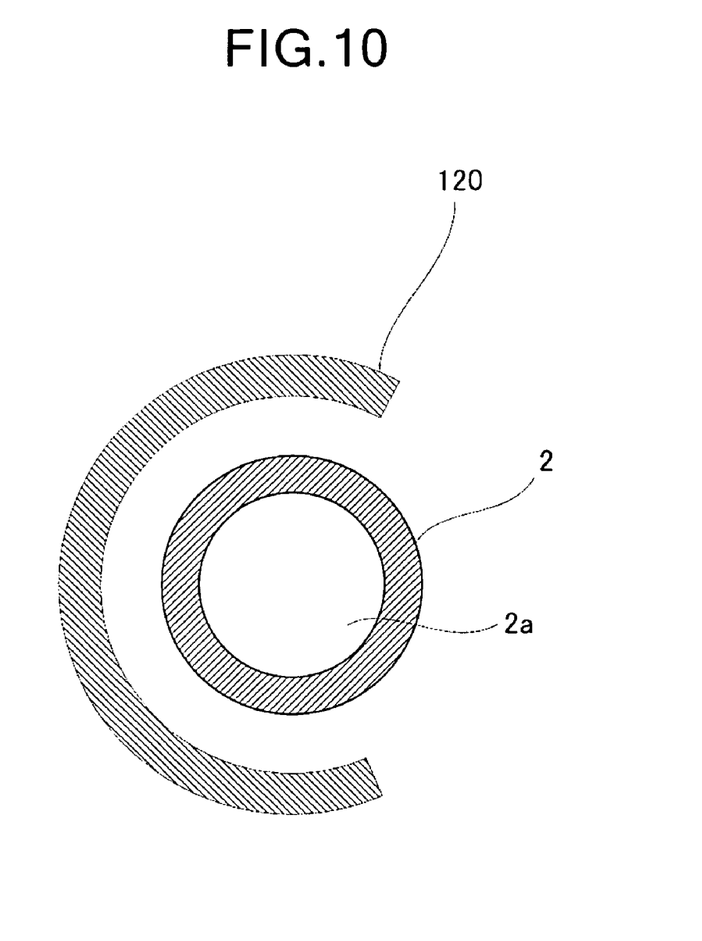
FIG. 10 is a sectional view illustrating a piercer having a substantially C-letter shaped cross-section.

Examples of the piercer capable of forming the deformation piece in the lid include, other than the one having the substantially L-letter shape in section shown in FIG. 7, those having other shapes in section such as a piercer 120 having a substantially C-letter shape in section (see FIG. 10).

The foregoing detailed description and accompanying drawings have been provided by way of explanation and illustration, and are not intended to limit the scope of the appended claims. Many variations in the present embodiments illustrated herein will be obvious to one of ordinary skill in the art, and remain within the scope of the appended claims and their equivalents.

What is claimed is:

1. A liquid sample suctioning device for suctioning a liquid sample in a container comprising a lid, comprising:
  a piercer having a leading end insertable into the container by piercing through the lid and forming a deformation piece deformable toward an inner side of the container in the lid;
  a pipette configured for suctioning the liquid sample in the container;
  a first driving part for moving up and down the piercer; and
  a second driving part for moving up and down the pipette along the piercer;
    wherein a cross-section of the piercer perpendicular to a longitudinal axis thereof has a geometry configured to receive the pipette, and wherein the piercer comprises a bent metal plate that is bent along a longitudinal direction thereof and comprises a non-pipe shape.

2. The liquid sample suctioning device according to claim 1, wherein the geometry is a substantially L-letter or C-letter shape.

3. The liquid sample suctioning device according to claim 1, wherein the second driving part moves down the pipette while the piercer pierces through the lid.

4. The liquid sample suctioning device according to claim 2, wherein the pipette is guided by the piercer when the second driving part moves down the pipette.

5. The liquid sample suctioning device according to claim 1, wherein a leading end of the pipette is formed in a tapered shape.

6. A liquid sample suctioning device for suctioning a liquid sample in a container comprising a lid, comprising:
  a first piercer having a leading end insertable into the container by piercing through the lid and forming a slit in the lid;
  a second piercer comprising a needle part configured for piercing the lid at a leading end thereof and for suctioning the liquid sample in the container;
  a first driving part for moving up and down the first piercer; and
  a second driving part for moving up and down the second piercer;
    wherein the second piercer is guided by the first piercer when the second driving part moves down the second piercer.

7. The liquid sample auctioning device according to claim 6, wherein the second driving part moves down the second piercer while the first piercer pierces through the lid.

8. A liquid sample suctioning device for auctioning a liquid sample in a container comprising a lid, comprising:
   a piercer having a leading end insertable into the container by piercing through the lid and forming a linear slit in the lid;
   a pipette configured to be inserted into the container and suction the liquid sample in the container;
   a first driving part for moving up and down the piercer; and
   a second driving part for moving up and down the pipette when the piercer pierces through the lid;
   wherein the piercer comprises a plate-like shape.

9. The liquid sample suctioning device according to claim 8, wherein a leading end of the pipette is formed in a tapered shape.

10. An analyzer, comprising:
   a liquid sample suctioning unit for suctioning a liquid sample in a container comprising a lid; and
   an analyzing unit for analyzing the liquid sample suctioned by the liquid sample suctioning unit; wherein
   the liquid sample suctioning unit comprises:
      a piercer having a leading end insertable into the container by piercing through the lid and forming a deformation piece deformable toward an inner side of the container in the lid;
      a pipette configured for suctioning the liquid sample in the container;
      a first driving part for moving up and down the piercer; and
      a second driving part for moving up and down the pipette along the piercer;
      wherein a cross-section of the piercer perpendicular to a longitudinal axis thereof has a geometry configured to receive the pipette, and wherein the piercer comprises a bent metal plate that is bent along a longitudinal direction thereof and comprises a non-pipe shape.

11. The analyzer according to claim 10, wherein the geometry is a substantially L-letter or C-letter shape.

12. The analyzer according to claim 10, wherein the second driving part moves down the pipette while the piercer pierces through the lid.

13. The analyzer according to claim 12, wherein the pipette is guided by the piercer when the second driving part moves down the pipette.

14. The analyzer according to claim 10, wherein a leading end of the pipette is formed in a tapered shape.

15. An analyzer, comprising:
   a liquid sample auctioning unit for suctioning a liquid sample in a container comprising a lid; and
   an analyzing unit for analyzing the liquid sample suctioned by the liquid sample suctioning unit; wherein
   the liquid sample suctioning unit comprises:
      a first piercer having a leading end insertable into the container by piercing through the lid and forming a slit in the lid;
      a second piercer comprising a needle part configured for piercing the lid at a leading end thereof and for auctioning the liquid sample in the container;
      a first driving part for moving up and down the first piercer; and
      a second driving part for moving up and down the second piercer;
      wherein the second piercer is guided by the first piercer when the second driving part moves down the second piercer.

16. The analyzer according to claim 15, wherein the second driving part moves down the second piercer while the first piercer pierces through the lid.

17. An analyzer, comprising:
   a liquid sample suctioning unit for suctioning a liquid sample in a container comprising a lid; and
   an analyzing unit for analyzing the liquid sample suctioned by the liquid sample suctioning unit; wherein
   the liquid sample suctioning unit comprises:
      a piercer having a leading end insertable into the container by piercing through the lid and forming a linear slit in the lid;
      a pipette configured to be inserted into the container and suction the liquid sample in the container;
      a first driving part for moving up and down the piercer; and
      a second driving part for moving up and down the pipette when the piercer pierces through the lid;
      wherein the piercer comprises plate-like shape.

18. The analyzer according to claim 17, wherein a leading end of the pipette is formed in a tapered shape.

* * * * *

UNITED STATES PATENT AND TRADEMARK OFFICE
CERTIFICATE OF CORRECTION

PATENT NO. : 7,647,847 B2 Page 1 of 1
APPLICATION NO. : 11/516278
DATED : January 19, 2010
INVENTOR(S) : Kitagawa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 426 days.

Signed and Sealed this

Twenty-eighth Day of December, 2010

David J. Kappos
*Director of the United States Patent and Trademark Office*